United States Patent [19]

Flick

[11] Patent Number: 5,374,283

[45] Date of Patent: Dec. 20, 1994

[54] ELECTRICAL THERAPEUTIC APPARATUS

[76] Inventor: A. Bart Flick, P.O. Box 640, Highway 441 So., Demorest, Ga. 30535

[21] Appl. No.: 159,546

[22] Filed: Dec. 1, 1993

[51] Int. Cl.$^5$ .............................................. A61N 1/32
[52] U.S. Cl. ...................... 607/46; 607/152; 128/644
[58] Field of Search ............... 607/115, 140, 144, 152, 607/46; 128/644, 640, 639

[56] References Cited

U.S. PATENT DOCUMENTS

| | | |
|---|---|---|
| 1,498,059 | 6/1924 | Tyler . |
| 1,545,413 | 7/1925 | Elmvall . |
| 1,975,518 | 10/1934 | Rose . |
| 1,989,282 | 1/1935 | Kimble et al. . |
| 3,543,760 | 12/1970 | Bolduc . |
| 3,817,253 | 6/1974 | Gonser . |
| 3,845,771 | 11/1974 | Vise . |
| 3,911,906 | 10/1975 | Reinhold, Jr. . |
| 4,213,463 | 7/1980 | Osenkarski . |
| 4,240,437 | 12/1980 | Church . |
| 4,456,001 | 6/1984 | Pescatore . |
| 4,509,535 | 4/1985 | Bryan . |
| 4,510,939 | 4/1985 | Brenman et al. . |
| 4,528,265 | 7/1985 | Becker . |
| 4,554,923 | 11/1985 | Batters . |
| 4,556,051 | 12/1985 | Maurer ........................... 607/46 |
| 4,664,118 | 5/1987 | Batters . |
| 4,867,166 | 9/1989 | Axelgaard et al. . |
| 5,038,797 | 8/1991 | Batters . |
| 5,067,478 | 11/1991 | Berlant . |

FOREIGN PATENT DOCUMENTS 60925 2/1892 German Dem. Rep. .

OTHER PUBLICATIONS

Electrical Augmentation of the Antimicrobial Activity of Silver Nylon Fabrics, Andrew A. Marino, et al, Journal of Biological Physics vol. 12, 1984.
Electrochemical Properties of Siliver-Nylon Fabrics, Andrew A. Marino, et al. Electrochemical Science and Technology.

Primary Examiner—William E. Kamm
Assistant Examiner—Scott M. Getzow
Attorney, Agent, or Firm—Kennedy & Kennedy

[57] ABSTRACT

An electrical therapeutic apparatus (10) for the treatment of body pain and edema. The apparatus has an electrical pulse producing device (11) coupled to wrap (12) by conductor (13). The wrap is comprised of nylon coated with silver which forms an electrode. A second electrode (14) is coupled by conductors (15) to the device.

4 Claims, 3 Drawing Sheets

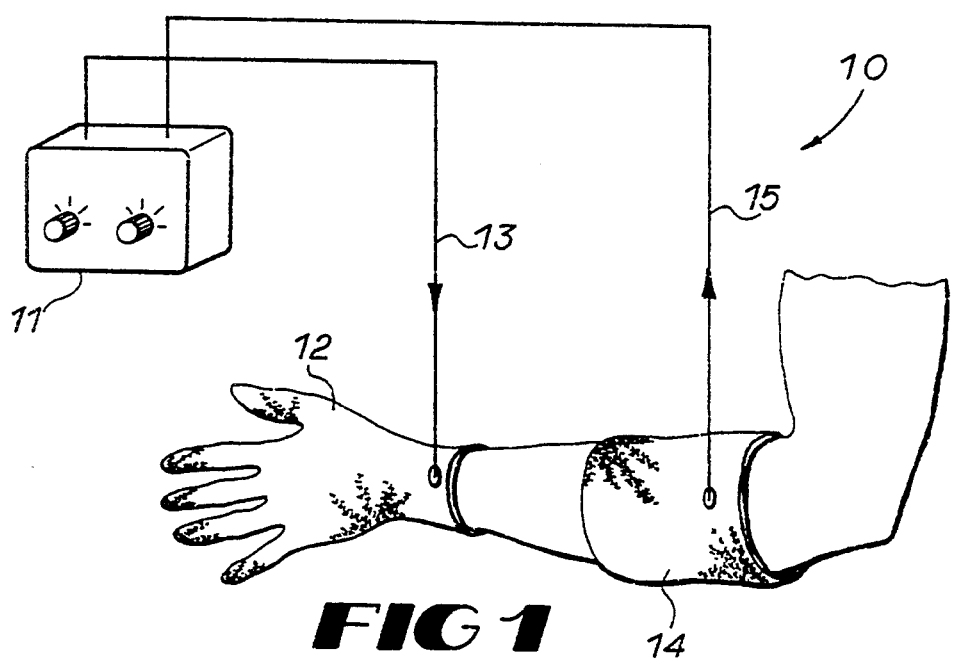
FIG 1
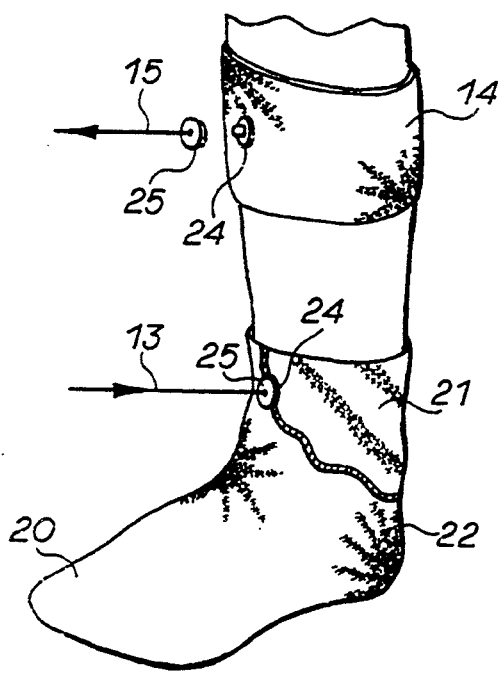
FIG 2
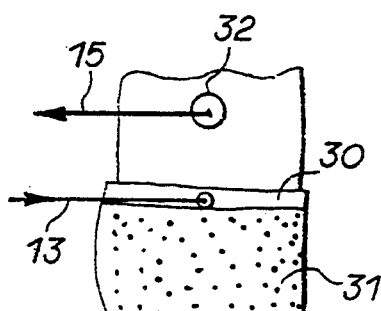
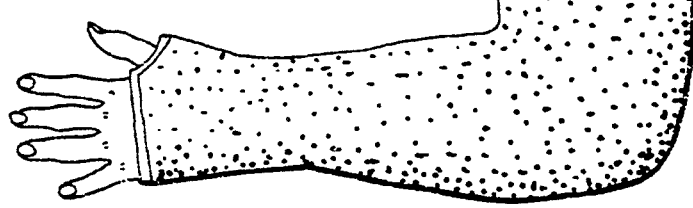
FIG 3

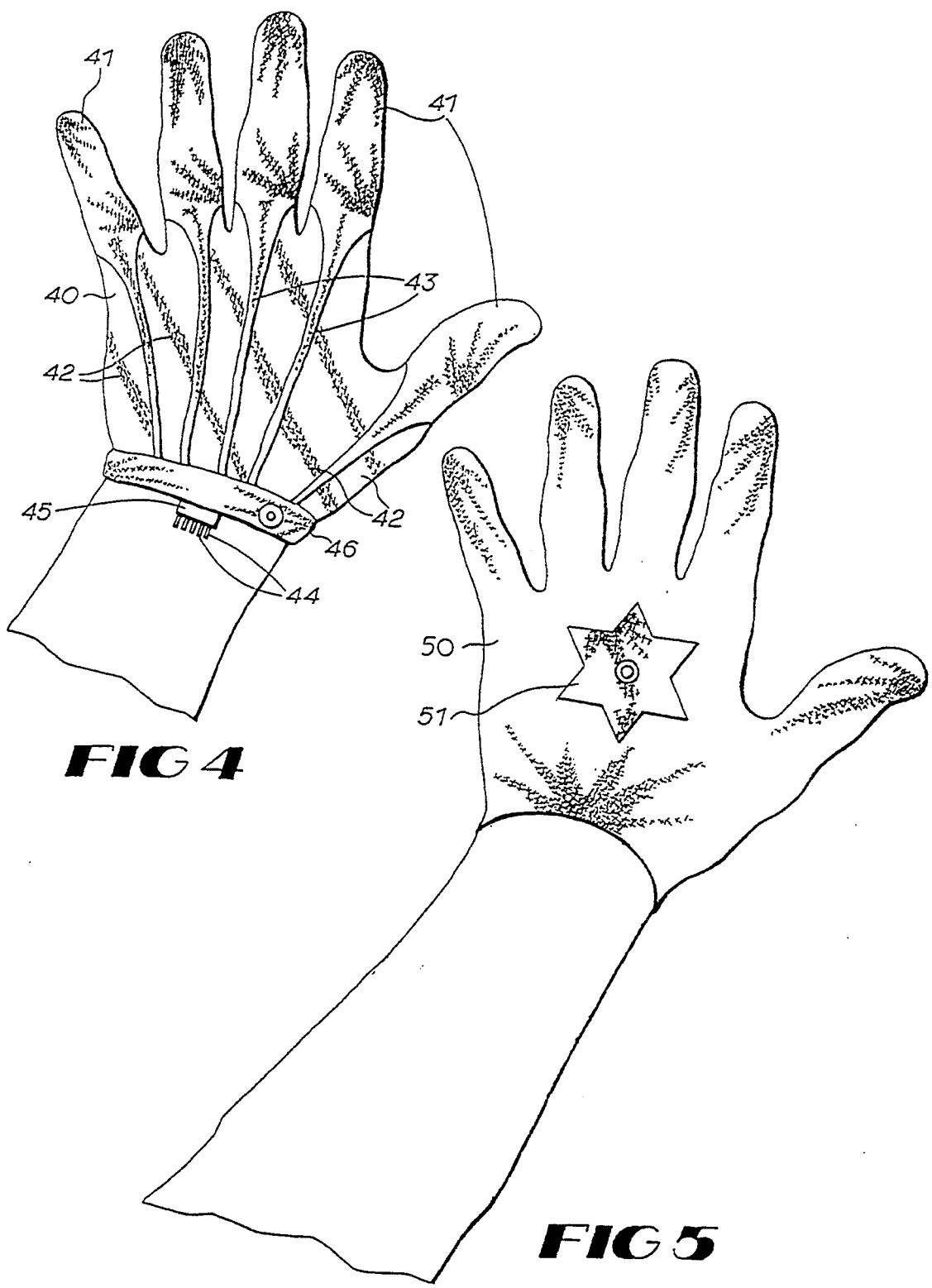

ELECTRICAL THERAPEUTIC APPARATUS

TECHNICAL FIELD

This invention relates to electrical therapeutic apparatuses for the treatment of edema and both localized and systemic medical problems such as pain, edema and inflammation.

BACKGROUND OF THE INVENTION

The use of electric shock pulses to control pain, stimulate muscles and treat edema and inflammation in the human body is well known. Electric shock pulses, which produce and electromagnetic field, are passed through the tissue to be treated by placing electrodes on the skin about the tissue to be treated. The electrodes must make good, continuous and uniform contact with the skin, otherwise electrical hot spots occur which may cause skin irritation or even skin burns.

Electrical therapeutic devices have been made which have electrodes comprised of metal plates and sponges which extend between the metal plates and the patient's skin. These sponges however must constantly be moistened with wet lubricant in order to avoid drying and to maintain good electric contact with the skin. The wet lubricant oftentimes causes the skin to become mottled or macerated during prolonged use. Furthermore, these types of electrodes are typically in the shape of small patches which do not conform well to body extremities such as the hands.

Devices have been devised which have electrodes comprised of a material of interlocked metal rings, as shown in U.S. Pat. Nos. 1,498,059 and 4,664,118. These electrodes are placed directly against the skin of a person. However, because the material is constructed of stiff, segmented components, here again it does not conform well to the extremities of the body such as the hands and feet. Furthermore, it does not have stretching capabilities to insure a snug, uniform fit about the extremity. This lack of body conformity results in an uncomfortable and inconsistent contact with the skin which may cause hot spots as well as an uneven distribution of the current through the underlying tissue.

Electrodes have also been made of metalized fabrics comprised of a woven nylon mesh coated with silver. As shown in U.S. Pat. No. 4,528,265 these metalized fabrics have been used to treat open wound lesions electrochemically be wetting the mesh with a saline solution and applying the wetted material directly to the open lesion. An electrical potential gradient forces silver ions to migrate from the metalized fabric into the body tissue. This has been found to cause cellular modifications to arrest multiplication of cancer cells and stimulate wound healing. Clinical medicine had previously recognized the antiseptic and antimicrobial properties of silver and the use of silver coated fabrics for silver donation as described in "*Electrochemical Properties of Silver-Nylon Fabrics*" by Andrew A. Marino, et al. in the January 1985 issue of Electrochemical Science and Technology. However, these have not been used for the treatment of pain and edema.

SUMMARY OF THE INVENTION

It has now been discovered that non-conductive fabric with a metallic coating may over substantial periods of time be used in the treatment of pain and edema without significant migration of metallic ions and with minimal depletion of metal from the fabric. This is done with an electrical therapeutic apparatus having a wrap made of flexible, non-conductive fabric shaped to overlay the skin of a body portion to be treated. The wrap has at least one section impregnated with metallic particles to form a first discontinuous electrode contactable with the skin of the body portion. The apparatus also includes a second electrode, means for applying the second electrode to the body portion spacially from the first electrode, and means for electrically coupling the electrode and the fabric section to an electric power source so as to establish a voltage through the body portion between the electrodes.

BRIEF DESCRIPTION OF THE DRAWING

FIG. 1 is a perspective view of an electrical therapeutic apparatus that embodies principles of the invention in a preferred form of a glove and a wrap.

FIG. 2. is a perspective view of an electrical therapeutic apparatus in another preferred form of a sock with a portion of an outer layer removed to show an internal layer.

FIG. 3. is a perspective view of the apparatus of FIG. 1 shown with a orthopaedic cast mounted thereabout.

FIG. 4 is a perspective view of an electrical therapeutic apparatus in another preferred form of a materially segmented glove.

FIG. 5 is a perspective view of an electrical therapeutic apparatus in another preferred form of a glove.

DETAILED DESCRIPTION

Figure 6:
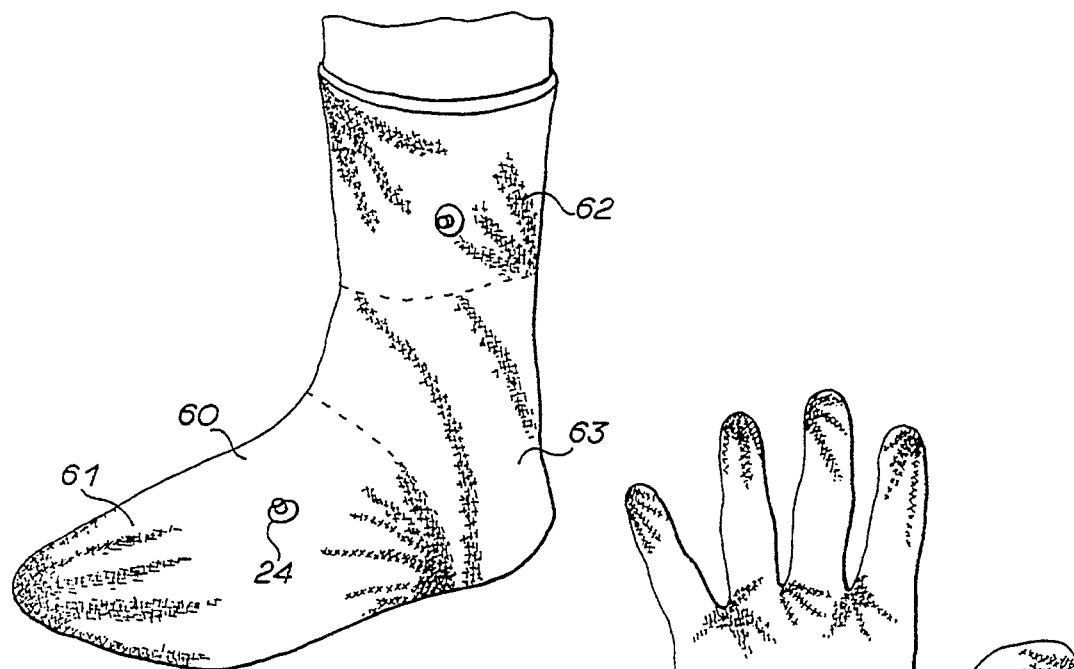
FIG. 6 is a perspective view of an electrical therapeutic apparatus in another preferred form of a sock.

With reference next to the drawings, there is shown in FIG. 1 an electric therapeutic apparatus 10 of the present invention. The apparatus 10 has an electrical pulse producing device 11 electrically coupled to a wrap 12 through a conductor 13. Wrap 12 is in the form of a glove and acts as an electrode. A second electrode 14 is electrically coupled to the pulse producing device 11 through a conductor 15. Electrode 14 is place about the forearm of a patient so as to be spaced from the glove shaped wrap 12. The electric pulse producing device 11 may be a portable pulsed galvanic stimulator.

The wrap 12 and electrode 14 are made of a woven, metalized fabric such as that manufactured by Swift Textile Metalizing Corporation of Bloomfield, Conn. or Polygenex International of Cary, N.C. The totally or partially metalized fabric is extremely pliable and comprised of woven or knitted nylon fibers that have been coated with silver crystals or a combination of coated nylon fibers and non-coated nylon fibers. The coating process does not affect the handling characteristics or strength of the material. The extreme pliability, flexibility and stretchability of the metalized fabric allows it to conform closely to underlying body tissues so as to provide a uniform electrical contact yet allow a free range of motion for the underlying portion of the body. Alternatively, the non-conductive fabric may be coated or embedded with particles of silver, gold, brass, stainless steel or other metals.

With material of this construction a patient may easily manipulate the joints and muscles underlying the wrap to increase circulation, decrease edema and speed the healing process. Additionally, because the fabric may conform to extremities better than those of the prior art used for electrical treatment of pain and edema, a more uniform current is passed to the tissue. Because of this a higher current may be used without causing electrical hot spots to occur between the wrap and the skin.

With reference to FIG. 1, an injured hand is shown donned with a glove shaped wrap 12 upon the hand and an electrode 14 wrapped about the forearm. A generally uniform electric current is passed throughout the glove so as to apply the current uniformly to the enveloped hand. The current is applied at a shock pulse rate sufficient to reduce pain and edema in the enveloped hand without causing thermal effects such as heat build-up within the tissue as, for example, 8 pulses per second with a 2 to 3 millisecond burst of 1 to 100 volts with an extremely low amperage. The current may be either AC. or DC.

With reference next to FIG. 2, a wrap 20 of alternative form is shown in the configuration of a sock made of a layer of metalized fabric 21 with an overlaying layer of electrically insulative fabric 22. The insulative fabric 22 prevents the unwanted discharging of the current along the outer surface of the metalized fabric 21. It should be understood that the overlaying electric insulating fabric described may be applied to any of the other embodiments of the invention herein described. Wrap 20 and electrode 14 each have an electrically connected male coupler 24 which is releasable coupled to a female coupler 25 which is electrically connected to the ends of corresponding conductors 13 and 15. Wrap 20 is used for the treatment of the foot, ankle and lower leg.

With reference next to FIG. 3, a wrap 30 of alternative form is shown. Wrap 30 is made of metalized fabric which is placed about an arm that is then wrapped with an orthopaedic cast 31 so that the wrap acts as both a therapeutic electrode and a cast liner. A small electrode 32 is mounted to the skin of the patient spatially from electrode 30. It should however be understood that a metalized fabric electrode similar to electrode 14 shown in FIG. 1 or any electrode described herein may also be used in place of electrode 32. Here, the wrap and electrode reduce pain and speed the healing process associated with broken bones and immobilized portions of body.

With reference next to FIG. 4, there is shown a glove shaped wrap 40 having fingers 41 made of metalized fabric. The fingers 41 are separated from each other by electrically insulative fabric 42. Each finger 41 has an elongated extension 43 of metalized fabric which couples the finger to a prong 44 of a five prong male jack 45. Jack 45 is coupled to an unshown corresponding female jack with five conductors coupled to the electrical pulse producing device 11 so that each finger 41 may be controlled as a single electrode. A metalized fabric wrist band 46 forms a second electrode made of metalized fabric. The wrist band electrode 46 is electrically insulated from fingers 41 and their corresponding extensions 43. Wrap 40 is used not only for the direct treatment of individual fingers but also for the treatment of remote or systemic body pain and biological functions, as the fingers are believed to be access points to influence the entire body. For example, it has been found that a muscle tension headache may be relieved by applying a current to the middle finger or the first web space dorsally on the hand. It should be understood that preferably the glove shaped wrap includes an unshown layer of insulative fabric overlying the metalized fabric to prevent electrical shorts between adjacent portions of metalized fabric.

With reference next to FIG. 5, there is shown a glove shaped wrap 50 having a star-shaped electrode 51 overlying the back of a hand and a similarly oriented, unshown star-shaped electrode overlying the palm of the hand. Electrode 51 and the palm side electrode are made of metalized fabric which are separated from each other by electrically insulative fabric 42. The shaping of the electrode allows the electric current to be concentrated over specific portions of the body. For example an inflammation of the extensor tendons to the thumb, commonly referred to as DeQuervains Tenosynovitis, can be treated by forming the electrodes so as to overlie the inflamed tendons and along the opposite side of the hand.

With reference next to FIG. 6, there is shown a sock shaped wrap 60 having a toe portion electrode 61 and a leg portion electrode 62 made of metalized fabric. Wrap 60 also has an ankle portion 63 made of electrically insulative fabric. This wrap is used for the treatment of the foot, ankle and lower leg.

Figure 7:
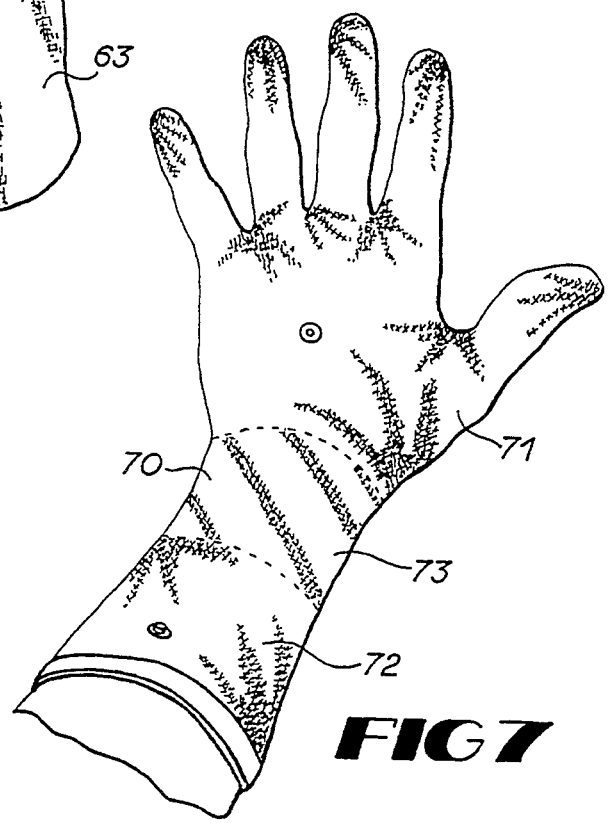
FIG. 7 is a perspective view of an electrical therapeutic apparatus in still another preferred form of a glove.

With reference next to FIG. 7, there is shown another glove shaped wrap 70 in an alternative form. Here the wrap 70 has a hand electrode 71 and a forearm electrode 72 separated from each other by a middle portion 73 made of an electrically insulative fabric. The wrap also has an unshown inner layer of electrically resistive fabric to prevent direct contact between the skin and the electrodes 71 and 71. This wrap affects the body by producing a weak electromagnetic field which creates a very gentle stimulus to the surrounding tissues, i.e. indirect contact with the skin. Wrap 70 is used for the treatment of the hand, wrist and forearm.

Figure 8:
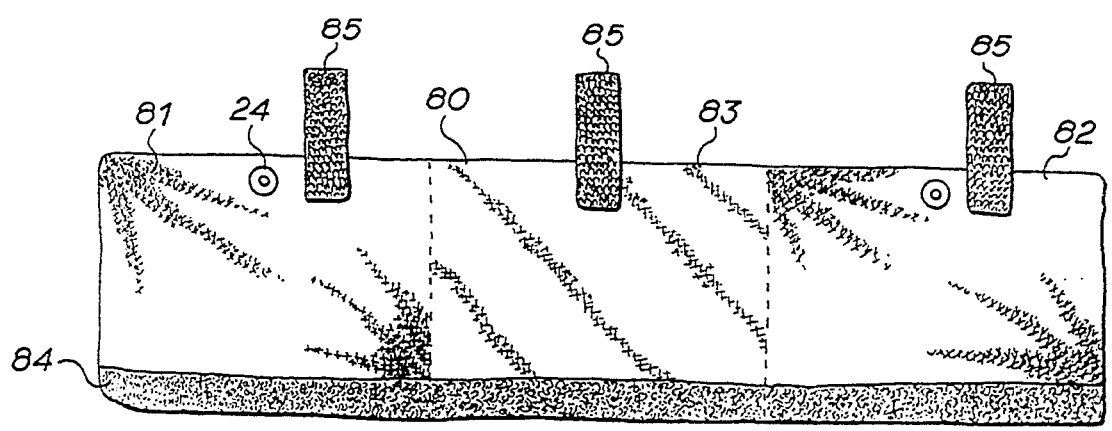
FIG. 8 is a perspective view of an electrical therapeutic apparatus in yet another preferred form of a strap.

With reference next to FIG. 8, there is shown yet another alternative form of the invention in the form of a rectangular sheet 80. The sheet 80 has end portion electrodes 81 and 82 made of metalized fabric and a middle portion 83 of electrically insulative fabric extending between electrodes 81 and 82. The sheet also has an elongated strip of Velcro fastening material 84 along one edge of the electrodes and middle portion 83 which releasably mates with three Velcro hook type fasteners 85 mounted along an opposite edge. The sheet 80 may be place on an appendage, such as a leg, by simply wrapping it about the appendage and securing it in place with fasteners 84 and 85.

Figure 9:
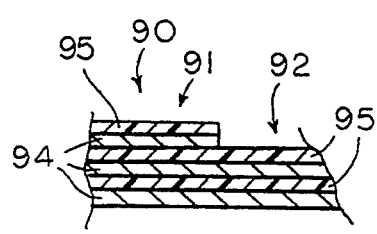
FIG. 9 is a cross sectional view of a portion of a wrap.

With reference next to FIG. 9, there is shown a portion of a wrap 90. The wrap 90 has a first portion 91 and a second portion 92. The first portion 91 has three layers of metalized fabric 94 separated by layers of electrically insulative fabric 95, while the second portion 92 has two layers of metalized fabric 94 separated by layers of electrically insulative fabric 95. The first and second portions 91 and 92 have different electromagnetic characteristics as a result of the number of metalized layers. The difference is the electromagnetic field creates electromagnetic gradients which allow the distribution, concentration and intensity of the electromagnetic field to be controlled to a higher degree. It should be understood that the wrap may be made of any combination of any number of layers of metalized fabric in this manner.

From the foregoing it is seen that an electrical therapeutic apparatus for the treatment of edema and body pain through the use of electrical currents applied to the skin through electrodes is now provided which overcomes problems associated with those of the prior art. It should be understood however that the just described embodiment merely illustrates principles of the invention in its preferred form. Many modifications, additions and deletions may, in addition to those expressly recited, be made thereto without departure from the spirit and scope of the invention as set forth in the following claims.

I claim:

1. An electrical therapeutic apparatus for the treatment of localized and systemic body pain and edema comprising a flexible, non-conductive fabric shaped to overlay the skin of a body portion to be treated, said fabric having at least one section impregnated with metallic particles to form a first discontinuous electrode contactable with the skin of the body portion, an insulative layer of material mounted to said fabric, and another layer of non-conductive fabric having at least one section impregnated with metallic particles mounted to said insulative layer opposite said metallic particle impregnated section of said non-conductive fabric; a second electrode; means for applying said second electrode to the body portion spacially from said first electrode; and means for electrically coupling said electrodes to an electric power source so as to establish a voltage through the body portion between said electrodes.

2. An orthopaedic cast and electrical therapeutic apparatus for the treatment of localized and systemic body pain and edema comprising a flexible, non-conductive fabric shaped to overlay the skin of a body portion to be treated, said fabric having at least one section impregnated with metallic particles to form a first discontinuous electrode contactable with the skin of the body portion, an orthopaedic cast mounted about said fabric; a second electrode; means for applying said second electrode to the body portion spacially from said first electrode; and means for electrically coupling said electrodes to an electric power source so as to establish a voltage through the body portion between said electrodes.

3. An electrical therapeutic apparatus for the treatment of localized and systemic body pain and edema comprising a flexible, non-conductive fabric in the form of a glove shaped to overlay the skin of a body portion to be treated, said fabric having at least one section impregnated with metallic particles to form a first discontinuous electrode contactable with the skin of the body portion; a second electrode; means for applying said second electrode to the body portion spacially from said first electrode; and means for electrically coupling said electrodes to an electric power source so as to establish a voltage through the body portion between said electrodes.

4. An electrical therapeutic apparatus for the treatment of localized and systemic body pain and edema comprising a flexible, non-conductive fabric in the form of a sock shaped to overlay the skin of a body portion to be treated, said fabric having at least one section impregnated with metallic particles to form a first discontinuous electrode contactable with the skin of the body portion; a second electrode; means for applying said second electrode to the body portion spacially from said first electrode; and means for electrically coupling said electrodes to an electric power source so as to establish a voltage through the body portion between said electrodes.

* * * * *